US006558911B1

(12) United States Patent
Sutovsky

(10) Patent No.: US 6,558,911 B1
(45) Date of Patent: May 6, 2003

(54) SPERM QUALITY ASSAY

(75) Inventor: Peter Sutovsky, Aloha, OR (US)

(73) Assignee: Oregon Health Sciences University, Portland, OR (US)

(*) Notice: Subject to any disclaimer, the term of this patent is extended or adjusted under 35 U.S.C. 154(b) by 0 days.

(21) Appl. No.: 09/460,325

(22) Filed: Dec. 10, 1999

(51) Int. Cl.[7] .......................... G01N 33/567; G01N 1/02
(52) U.S. Cl. ............................ 435/7.2; 435/2; 435/7.2; 435/7.21; 435/7.92; 435/7.94; 435/287.2; 435/325; 435/375; 435/967; 436/63; 436/65; 436/172; 436/548; 436/808; 436/814; 536/24.31
(58) Field of Search ............................ 435/2, 7.1, 7.2, 435/7.21, 7.9, 7.92, 7.94, 29, 183, 243, 287.2, 320.1, 254.2, 325, 375, 967; 436/63, 65, 172, 536, 546, 548, 800, 808, 814; 536/23.2, 23.1, 23.5, 24.31

(56) References Cited

U.S. PATENT DOCUMENTS

| | | | |
|---|---|---|---|
| 4,444,879 A | * 4/1984 | Foster et al. ................... 435/7 |
| 4,683,213 A | 7/1987 | Ax .............................. 436/501 |
| 4,946,778 A | 8/1990 | Ladner et al. .............. 435/69.6 |
| 5,270,163 A | 12/1993 | Gold et al. ................... 435/6 |
| 5,475,096 A | 12/1995 | Gold et al. ................ 536/23.1 |
| 5,753,231 A | 5/1998 | Herr et al. ................ 424/185.1 |
| 6,087,122 A | * 7/1999 | Hustad et al. ............... 435/29 |
| 5,962,241 A | 10/1999 | Ax et al. .................... 435/7.92 |
| 5,976,849 A | * 11/1999 | Hustad et al. .............. 435/183 |

FOREIGN PATENT DOCUMENTS

| WO | WO 93/03367 | 2/1993 |
|---|---|---|
| WO | WO 97/38134 | 10/1997 |
| WO | WO 98/33941 | 8/1998 |
| WO | WO 99/07724 | 2/1999 |

OTHER PUBLICATIONS

Chen et al. Ubiquitination of Histone H3 in elongating spermatidsof rat testes, Journal of Biological Chemistry, 273 (21): 13165–13169 (1998).*
Lippert et al., immunoreactive ubiquitin in human seminal plasma, Journal of Andrology, 14 (2): 130–131 (Mar.–Apr. 1993).*
Varshasky, Genes Cells 2: 13–28 [1997].
Amann, J. Androl. 10(2):89–98 [1989].
Köhlr and Milstein, Nature 256:495–497 [1975].
Engvall, Methods in Enzymology, 70:419 [1980].
Scharpe et al., Clin. Chem. 22:733 [1976].
Wisdom, Clin. Chem. 22:1243 [1976].
Hermo et al., Am. J. Anat. 183:107–124 [1988].
Ramamohana et al., Theriogenology 14:1–12 [1980].
Roussel et al., Fertil. Steril. 18:509–516 [1967].
Wilkinson et al., J. Biol. Chem., 256:9235 [1981].
Kozbor et al. Immunol. Today 4:72 [1983].
Cole et al., in *Monoclonal Antibodies and Cancer Therapy*, Alan R. Liss, Inc., pp. 77–96 [1985].
Cote et al., Proc. Natl. Acad. Sci. U.S.A.80:2026–2030 [1983].

Huse et al., Science 246:1275–1281 [1989].
Parrish et al., Theriogenology 25:591–600 [1986].
Cooper, et al., Cell Tissue Res. 256, 567–572 [1989].
Szczygiel and Kurpisz, Andrologia 31:63–75 [1999].
Ciechanover, Cell 79:13–21 [1994].
Weil et al., J. Cell Sci. 111:2707–2715 [1998].
Yin et al., Dev. Biol. 204:165–171 [1998].
Sakkas et al., Exp. Cell Res. 251:350–355 [1999].
Adonian and Hermo, J. Androl. 20:415–429 [1999].
Igdoura et al., Microsc. Res. Tech. 29:468–480 [1994].
Coux et al., Ann. Rev. Biochem. 65:801 [1996].
Rozakis–Adcock et al., J. Biol. Chem. 266:16476 [1990].
McCoy, *Flow Cytometry and Clinical Diagnosis*, Karen et al., eds., ASCP Press, Chicago, p. 26–55 [1994].
Moore et al., Fertil. Steril. 58, 776–783 [1992].
Sutovsky et al., Human Reprod., 14: 2301–2312 [1999].
Fraile et al., Biol. Reprod. 55: 291–297 [1996].
Lippert et al., J. Androl. 14: 130–131 [1993].
Sutovsky et al., "Sperm mitochondrial Ubiquitination and a Model Explaining the Strictly Maternal mtDNA Inheritance in Mammals," Mol. Biol. Cell., 9 suppl., 309a.
Sutovsky et al., "Ubiquitin Tag for Sperm Mitochondria," Nature 402:371–2 (1999).
Rivkin et al., "A Protein Associated with the Manchette During Rat Spermiogenesis is Encoded by a Gene of the TBP–1–Like Subfamily with Highly Conserved ATPase and Protease Domains," Molecular Reproduction and Development 47:77–89 (1997).
Kruger et al., "New Method of Evaluating Sperm Morphology with Predictive Value for Human In Vitro Fertilization," Urology, 30:248–51 (1984).
Moilanen et al., "Flow Cytometric Analysis of Semen Preparation, and Assessment of Acrosome Reaction, Reactive Oxygen Species Production and Leucocyte Contamination in Subfertile Men," Andrologia 31: 269–276 (1999).
Hacker–Klom et al., "DNA Flow Cytometry of Human Semen," Human Reproduction 14:2506–2512 (1999).
Tomlinson et al., "The Diagnostic and Prognostic Value of Traditional Semen Parameters," J. Andrology 29:588 (1999).
Ferrari et al., "Chromatin Cytophotometric Analysis of Abnormal Bovine Spermatozoa," Andrologia 30:85–89 (1998).
Chen et al., "Ubiquitination of Histone H3 in Elongating, Supermadtids of Rat Testes," J. of Biological Chem. 273:13165–13169 (1998).

* cited by examiner

*Primary Examiner*—Long V. Le
*Assistant Examiner*—Gailene R. Gabel
(74) *Attorney, Agent, or Firm*—Medlen & Carroll, LLP

(57) ABSTRACT

The present invention relates to male infertility, and in particular to assays for predicting fertility in animals including human and bovines. In some embodiments, semen samples are evaluated by measuring the amount of ubiquitin in the sample, and in particular by measuring the extent of ubiquitination spermatozoa. Increased levels of ubiquitination in a sample are correlated with lower fertility. Ubiquitination may be assayed by several methods, including immunocytochemical measurement, ELISA, and flow cytometry.

24 Claims, No Drawings

SPERM QUALITY ASSAY

FIELD OF THE INVENTION

The present invention relates to male infertility, and in particular to assays for determining fertility.

BACKGROUND OF THE INVENTION

Infertility is diagnosed as the failure to become pregnant after one year of regular, unprotected intercourse. About ten percent of couples are infertile. Male factor infertility is the sole or contributing cause in about forty percent of these cases. In 1995, approximately 60,000 cycles of ART (Advanced Reproductive Technology) were performed in the United States to treat infertility. Of these procedures, approximately 90% involved in vitro fertilization at an average cost of $7,800.00 per cycle.

Semen analysis forms the basis of the initial evaluation for assessing male-factor. infertility. In general, two to three semen analyses are performed because semen quality normally fluctuates for a given individual. Subjects are normally encouraged to refrain from intercourse for 2 to 3 days prior to evaluation. Abstinence for a shorter time can decrease ejaculate volume, while prolonged abstinence can impair sperm motility. Traditional semen analysis evaluates a number of parameters, including, ejaculate volume, sperm count, sperm motility, forward progression, sperm morphology, pH, agglutination, leukospermia, and viscosity.

Sperm morphology is recognized as an important factor in semen analysis because it is a reflection of spermatogenic development. Traditionally, sperm have been classified according to the following morphologies: oval, amorphous, tapered, duplicated, and inrnature. However, determination of the percentage of normal spermatozoa with good morphology is highly subjective, and it is difficult to identify critical sperm morphological features that are responsible for fertility potential (Szczygiel and Kurpisz, Andrologia 31:63–75 [1999]). Additionally, in some instances, infertile men have sperm with apparently normal morphology. Furthermore, the results can be biased by damage incurred during normal preparation of the sperm for analysis (e.g., pipetting, centrifugation, and washing).

It is recognized that the identification of sperm abnormalities not apparent from semen analysis may lead to more appropriate and informed treatment plans for infertility (Szczygiel and Kurpisz, supra). However, there have been few recent efforts to develop methods that provide reliable prediction of fertility or fecundity based on sperm characteristics (Amann, J. Androl. 10(2):89–98 [1989]). Accordingly, what is needed in the art are objective semen quality assays that correlate to male factor infertility in the absence of morphological data suggesting otherwise, and that are unaffected by handling of the sample. It is desirable that such assays should be indicative of fertility.

SUMMARY OF THE INVENTION

The present invention relates to male infertility, and in particular to assays for determining fertility. In some embodiments of the present invention, methods for predicting fertility are provided. Accordingly, in some embodiments of the present invention, a method is provided for assaying fertility in an animal comprising a) providing a semen sample containing sperm; and b) measuring the amount of ubiquitin in the sample, wherein the amount of ubiquitin is indicative of fertility.

The present invention is not limited to a semen sample from a particular source. Indeed, it is contemplated that a variety of semen samples may be assayed. In some embodiments, the semen sample is obtained from a variety of animals, including, but not limited to, humans, cattle, sheep, pigs, horses, buffalo, bison and other domesticated and non-domesticated animals. In other embodiments, the sample is obtained by ejaculation, electroejaculation, or from the epididymis.

In other embodiments, the method of the present invention further comprises the steps of c) providing an antibody that binds to ubiquitin; and d) combining the semen sample with the antibody under conditions wherein the antibody binds to ubiquitihated sperm.

The present invention is not limited to any particular ubiquitin antibody. In some embodiments, the ubiquitin antibody is a polyclonal antibody, while in other embodiments, the ubiquitin antibody is a monoclonal antibody. In some particularly preferred embodiments, the antibody is selected from MAB 1510, AB 1690, Ubi-1, MK-11-3, MK-12-3, UCBA798/R5H, KM691, UG 9510, and U-5504.

The present invention is not limited to any particular technique for measuring ubiquitin or the degree of ubiquitination of sperm in the semen sample. Indeed, a variety of methods of determining the degree of ubiquitination are contemplated. In some embodiments, ubiquitination is assayed by immunocytochemical techniques wherein sperm that bind a labelled ubiquitin antibody are quantified. The present invention is also not limited to any particular method of quantitation. In some embodiments, the number of sperm within a given sample that are ubiquitinated is determined microscopically by counting the number of labelled sperm in at least one subsample of the semen sample. In other embodiments, the number of labelled sperm in a given sample is determined using a videoanalysis system in conjunction with fluorescence microscopy. In other embodiments, ubiquitination is assayed by immunocytochemical techniques, wherein sperm are sequentially exposed to a ubiquitin antibody and a labelled second antibody that binds to the ubiquitin antibody. In other embodiments of the present invention, flow cytometry is used to measure ubiquitin in a semen sample. In still further embodiments, the amount of ubiquitin in a semen sample is measured by enzyme-linked immunosorbant assay (ELISA).

The present invention is not limited to any particular labelled first or second antibodies. Indeed a variety of second antibodies are contemplated, including, but not limited to those labelled with fluorescent compounds (e.g., fluorescein, rhodamine), enzymatic markers (e.g., alkaline phosphatase, horseradish peroxidase), and colloidal gold.

In other embodiments, the present invention provides methods for assaying fertility in an animal. In some embodiments, the method comprises a) providing i) a test semen sample containing sperm; and ii) an antibody that binds to ubiquitin; b) combining the semen sample with the antibody under conditions wherein the antibody binds to ubiquitinated sperm; c) measuring the amount of ubiquitin in the sample; and, d) comparing the measured amount of ubiquitin in the sample with an amount of ubiquitin in a control sample from a donor of known fertility, wherein a greater amount of ubiquitination in the test semen sample as compared to the control sample is indicative of infertility.

In still other embodiments, the present invention provides kits for assaying sperm quality. In some embodiments, the kit comprises a) a first container containing an antibody that binds to ubiquitin; and b) a second container containing a control semen sample from a donor of known fertility. In further embodiments, the kit comprises an antibody that binds to the ubiquitin binding antibody. In still further embodiments, the kit comprises a labelled second antibody that binds to the antibody that binds ubiquitin. In other embodiments, the kit further comprises instructions for assaying fertility or sperm quality in an animal.

DEFINITIONS

To facilitate an understanding of the present invention, a number of terms and phrases are defined below:

As used herein, the term "ubiquitin" refers to a relatively small protein (approximately 76 amino acid residues) found in all cells of higher organisms (See e.g., Ciechanover, Cell 79: 3–21 [1994], incorporated herein by reference) and other ubiquitin-like proteins sharing homology with ubiquitin. In preferred embodiments, ubiquitin and ubiquitin-like molecules will be recognized by the following antibodies: MAB 1510, AB 1690, Ubi-1, MK-11-3, MK-12-3, UCBA798/ R5H, KM691, UG 9510, U-5504, P4D1 (Covance, Richmond, Calif.), 221M (Biomedia, Foster City, Calif.); 1 471 732 (Boehringer Mannheim, Indianapolis, Ind.), IB3 (Calbiochem, San Diego, Calif.); Z0458 (Dako Corp., Carpinteria, Calif.); NCL-UBIQ and NCL-UBIQm Novocastra (Novocastra, Newcastle upon Tyme, UK; Distributed in U.S. by Vector Labs Inc., Burlingame, Calif.), Ub(N-19), Ub(P1A), and Ub(C-20) (Santa Cruz Biotechnology Inc., Santa Cruz, Calif.), Ub(P1A) Santa Cruz Biotechnology Inc., Santa Cruz, Calif.), and 1B4-UB (Serotech Inc., Raleigh, N.C.).

As used, herein, the term "fertility" refers to the ability to conceive within one year of beginning unprotected intercourse.

As used herein, the term "infertility" refers to the inability to conceive after a year of unprotected intercourse.

As used herein, the term "semen sample" refers to any material containing sperm, whether processed or unprocessed, and includes ejaculates, electroejaculates, sperm isolated from testes or epididymes extended semen, sperm prepared by swim-up procedures, and sperm prepared by percoll gradient centrifugation.

As used herein, the term "measuring" refers to the act of determining the dimensions, quantity, or capacity of a material. When used in reference to ubiquitination of sperm in a sample, the term "measuring" encompasses determining the total amount of ubiquitin in a sample as well as determining the percentage or proportion of sperm that are ubiquitinated.

As used herein the term "antibody" refers to a glycoprotein evoked in an animal by an immunogen (antigen). An antibody demonstrates specificity to the antigen, or, more specifically, to one or more epitopes contained in the immunogen. Native antibody comprises at least two light polypeptide chains and at least two.heavy polypeptide chains, including, but not limited to IgG, IgM, IgA, IgE, and IgD. Each of the heavy and light polypeptide chains contains at the amino terminal portion of the polypeptide chain a variable region (i.e., $V_H$ and $V_L$. respectively), which, contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "$C_L$ region," and the constant region of the heavy chain is referred to as the "$C_H$ region." The constant region of the heavy chain comprises a $C_{H1}$ region, a $C_{H2}$ region, and a $C_{H3}$ region. A portion of the heavy chain between the $C_{H1}$ and $C_{H2}$ regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions.

As used herein, the term "enzyme-linked immunosorbant assay" refers to an immunoassay in which the amount of an antigen (e.g., ubiquitin) in a sample is quantitated by methods including, but not limited to, sandwich assays, competitive assays, and direct screening assays, and indirect assays (See e.g., Engvall, Methods in Enzymology, 70:419 [1980]; Scharpe et al., Clin. Chem. 22:733 [1976]; Schuurs et al., Immunoassay 1:229 (1980); Wisdom, Clin. Chem. 22:1243 [1976]).

As used herein, the term "flow cytometry" refers to an assay in which the proportion of a material (e.g., ubiquitinated sperm) in a sample is determined by labelling the material (e.g., by binding a labelled antibody to the material), causing a fluid stream containing the material to pass through a beam of light, separating the light emitted from the sample into constituent wavelengths by a series of filters and mirrors, and detecting the light.

As used herein, the term "quantitating" refers to the act of determining the amount or proportion of a substance (e.g., ubiquitin or ubiquitinated sperm) in a sample.

As used herein, the term "ubiquitinated sperm" refers to sperm that contain one or more ubiquitin molecules conjugated to one or more proteins of the sperm that are not generally ubiquitinated or display low levels of ubiquitination in a normal sperm (i.e., sperm of normal morphology and physiology).

As used herein, the term "subsample" refers to a sample population taken from a larger sample population.

As used herein, the phrase "indicative of fertility" refers to a trait that correlates to fertility or infertility.

As used herein, the phrase "control sample from a donor of known fertility" refers to a semen sample that has been previously characterized as possessing an amount of ubiquitin that is consistent with known fertility. The control sample can be characterized by a number of methods, including those described herein and U.S. Pat. Nos. 5,962, 241; 5,753,231; and 4,683,213, each of which is incorporated herein by reference. In one aspect, semen samples from known fertile.donors are within the definition. In another aspect, the control sample exhibits less ubiquitination than samples from infertile donors as measured by various quantitative techniques (e.g., ELISA, immunocytochemistry, or flow cytometry).

As used herein, the term "labelled second or secondary antibody" refers to an antibody that is conjugated to a detectable group (e.g., fluorochrome, enzyme, colloidal gold) or otherwise includes a detectable group (e.g., a radioisotope) and is capable of binding to another antibody. In preferred embodiments, the labelled secondary antibody binds to a primary antibody that is bound to an antigen of interest (e.g., ubiquitin).

DESCRIPTION OF THE INVENTION

The present invention relates to male infertility, and in particular to assays for determining fertility. Sexual reproduction by fertilization requires normal structure and flawless functioning of both male and female gametes. This is assured at multiple levels, including not only the selection of the fittest sperm at the egg vitellus during fertilization, but also the preselection of both sperm and eggs prior to their release from gonads. In mammals, female gametes, oocytes, undergo dramatic reduction in number, during which only a few oocytes from the initial pool are allowed to grow into full size and become ovulated. Meanwhile, the vast majority of oocytes along with their somatic entourage of ovarian follicular cells undergo atresia (e.g., an apoptotic process), encompassing a relatively well characterized cascade of cellular events. In contrast with our knowledge of oocyte selection, there are only a handful of reports implicating a role for apoptosis in the preselection of male gametes, spermatozoa. For example, components of an active apoptotic pathway were found in both the spermatogenic cell lines (reviewed by Hikim and Swerdloff, Rev. Reprod. 4(1):38–47 [1999]) and in the mature sperm of mice (Weil et al., J. Cell Sci. 111:2707–2715 [1998]; Yin et al., Dev. Biol. 204:165–171 [1998] and men (Sakkas et al., Exp. Cell Res. 251:350–355 [1999]), but a definitive mechanism for sperm quality control is yet to be established.

Following the exit from the testis via testicular rete, the mammalian spermatozoa undergo maturation and storage in the epididymis. The mammalian epididymis is composed of three distinct compartments, namely the caput, corpus, and cauda; each of which has a specific role in sperm maturation, sustenance, transport, and storage. A number of proteins secreted in apocrine fashion by epididymal epithelium, have been implicated in sperm immobilization, stabilization of sperm perinuclear structure and acquisition of fertilizing potential (Kirchhoff, Rev. Reprod. 3:86–95 [1998]). This important function of the epididymis protects sperm from oxidative damage during storage and after release into female genital tract. It has also been reported that the droplets of residual cytoplasm carried over from testis (Hermo et al., Am. J. Anat. 183:107–124 [1988]), and most of the abnormal spermatozoa (Ramamohana et al., Theriogenology 14:1–12 [1980]; Roussel et al., Fertil. Steril. 18:509–516 [1967]) are resorbed during sperm descent down the epididymis.

Currently, in the bovine artificial insemination industry, bulls are evaluated for fertility by a process that takes from five to six years to complete. When a breeder examines a one-year-old, sexually mature bull, the breeder's only source of information about the bull's fertility is the pedigree information available on the animal. Testicular size and other gross physical characteristics of the animal provide little or no useful information relating to fertility. Typically such a bull first is bred to cows until as many as 200 offspring are produced and monitored for milk production or some other quantitative trait. In the case of dairy cattle, it takes up to four years to do this, because the daughters themselves must become sexually mature so that they can be impregnated, calve, and begin to produce milk. If daughter milk production is good, the bull is kept and included in the breeder's general breeding program. Only at that time has the bull been bred to a population to a sufficiently large number of cows for the breeder to judge its fertility.

If a bull's fertility is found to be unacceptably low, the bull is culled. Typically, only one out of seven bulls are kept after this lengthy evaluation evaluation of the bull's progeny and fertility. In the meantime, the breeder has invested a large amount of money, time, and other resources to maintain and breed the bulls that are ultimately eliminated. Thus, detection and identification of bulls with low fertility at an early stage in the process provides considerable savings in time, money, and other resources.

It is not intended that the present invention be limited to particular mechanism of action. Indeed, an understanding of the mechanism is not necessary to make and use the present invention. However, the present inventors have discovered that the abnormal spermatozoa found in fertile males of several mammalian species including cattle and humans, are coated with ubiquitin or ubiquitin-like protein, a universal proteolytic marker, during epididymal passage. Furthermore, the degree of ubiquitination is correlated to fertility. Whereas a certain portion of the ubiquitinated defective sperm is resorbed before reaching the storage site in the cauda epididymis, other sperm are ejaculated and can be isolated from immotile sperm fraction. Therefore it appears that the ubiquitination of defective sperm may facilitate both their resorption prior to storage and immobilization prior to ejaculation. Thus, these mechanisms help prevent defective sperm from competing for an egg. These data are supported by the results of in situ investigations as well as by the reconstitution of this new epididymal function in vitro in the cultured epididymal epithelium. The finding of sperm ubiquitination in epididymis and its relationship to reproductive performance opens new possibilities for the diagnostics of male infertility, the evaluation of fertility, and may also offer new targets for contraceptives.

The following Description of the Invention is divided into the following topics: 1) Sources of Sperm for Analysis; 2) Antibodies Useful for Detection of Ubiquitin; 3) Methods for Quantifying Ubiquitination of Sperm; and 4) Fertility Assays.

1. Sources of Sperm for Analysis

The present invention provides methods for assaying fertility by determining the amount of ubiquitin in a semen sample (i.e., the degree of sperm ubiquitination). The method finds use in the analysis of semen samples from a variety of species (e.g., humans, bovines, primates, sheep, pigs, horses, rodents, camels, goats, bison, buffalo, llamas, foxes and ferrets). Furthermore, the samples may be collected by a variety of methods. In some embodiments of the present invention, the semen sample is from an ejaculate. In other embodiments, the semen sample is obtained by electroejaculation. In still other embodiments, the semen sample is obtained surgically from the epididymis. In some embodiments, the semen sample is analyzed without further processing except for preparation for flow cytometry, immunocytochemistry, or ELISA. However, in other embodiments, the sperm may be subjected to various preparation procedures known in the art (e.g., sperm swim-up or percoll gradient centrifugation).

2. Antibodies Useful for Detection of Ubiquitin

A variety of anti-ubiquitin antibodies are useful in the assays of the present invention. Examples of antibodies suitable for use in the present invention include, but are not limited to, MAB 1510 (Chemicon International, Inc. Temecula, Calif.); AB 1690 (Chemicon International, Inc. Temecula, Calif.); Ubi-1 (MAB1510) (Zymed Laboratories Inc., South San Francisco, Calif.); MK-11-3 (MBL Co, Ltd, Nagoya, Japan); MK-12-3 (MBL Co, Ltd, Nagoya, Japan); UCBA798/R5H (Accurate Chemical & Scientific Corp., Westbury, N.Y.); KM691 (Kamyia Biomedical Company, Seattle, Wash.); UG 9510 (Affiniti Research Products Ltd, Mamhead, UK); and U-5504 (Sigma, St. Louis, Mo.).

Alternatively, anti-ubiquitin antibodies are prepared as is known in the art using commercially available purified ubiquitin (Research Diagnostics, Inc., Flanders N.J.; See e.g., Ann. Rev. Biochem. 65:801 [1996]; J. Biol. Chem.

266:16476 [1990]; human ubiquitin 701-UB and 703-UB (R&D Systems, Minneapolis, Minn.); bovine ubiquitin U-6253, Sigma, St. Louis, Mo., Wilkinson et al., J. Biol. Chem., 256:9235 [1981]) to stimulate antibody production. The purified ubiquitin antigen finds use for the preparation of polyclonal, monoclonal, humanized, single chain and chimeric antibodies for use in the assays of the present invention. Thus, it is not intended that the present invention be limited to any particular type or class of antibody.

Various procedures known in the art may be used for the production of polyclonal antibodies to ubiquitin. For the production of antibody, various host animals can be immunized by injection with purified ubiquitin including but not limited to rabbits, mice, rats, sheep, goats, etc. In a preferred embodiment, the peptide is conjugated to an immunogenic carrier (e.g., diphtheria toxoid, bovine serum albumin (BSA) or keyhole limpet hemocyanin (KLH)). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward ubiquitin, any technique that provides for the production of antibody molecules by continuous cell lines in culture as known in the art may be used (See, e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies can be produced in germ-free animals (See e.g., PCT/US90/02545). According to the invention, human antibodies may be used and can be obtained by using any method known in the art, including, but not limited to human hybridomas (Cote et al., Proc. Natl. Acad. Sci. U.S.A.80:2026–2030 [1983]) or by transforming human B cells with EBV virus in vitro (Cole et al., in *Monoclonal Antibodies and Cancer Therapy*, Alan R. Liss, pp. 77–96 [1985]).

According to the invention, techniques described for the production of single chain antibodies (U.S. Pat. No. 4,946,778; herein incorporated by reference) can be adapted to produce ubiquitin-specific single chain antibodies. An additional embodiment of the invention utilizes the techniques described for the construction of $F_{ab}$ expression libraries (Huse et al., Science 246: 1275–1281 [1989]) to allow rapid and easy identification of monoclonal $F_{ab}$ fragments with the desired specificity for ubiquitin.

Antibody fragments that contain the idiotype (antigen binding region) of the antibody molecule can be generated by known techniques. For example, such fragments include but are not limited to: the $F_{(ab')2}$ fragment that can be produced by pepsin digestion of the antibody molecule; the $F_{ab'}$ fragments that can be generated by reducing the disulfide bridges of the $F_{(ab')2}$ fragment, and the $F_{ab}$ fragments that can be generated by treating the antibody molecule with papain and a reducing agent.

In some embodiments of the present invention, antibody binding is detected by detecting a label on the primary antibody. A variety of labels can be utilized depending on the nature of the assay. In some embodiments, the ubiquitin antibody is labelled with a fluorescent tag (e.g., fluorescein isothiocyanate, BODIPY, lucifer yellow, rhodamine isothiocyanate, texas red (sulfonyl chloride), lissamine rhodamine B, Cy3, Cy5, Cy7, allophycocyanin, cascade blue, succinimidyl esters of hydroxycoumarin, aminocoumarin, methoxycoumarin; these labels and their excitation and emission wavelengths are summarized in Table 1). In other embodiments, the ubiquitin antibody is labelled with an enzyme (e.g., alkaline phosphatase, horseradish peroxidase). In still further embodiments, the ubiquitin antibody is labelled with a radioactive tag (e.g., $^{125}I$, $^{35}S$, $^{3}H$) or colloidal gold. In other embodiments, the ubiquitin antibody is conjugated to biotin or strepavidin.

In other embodiments, the primary antibody is detected by detecting binding of a secondary antibody that recognizes the primary antibody (e.g., anti-mouse IgG, anti-mouse $IgG_1$, anti-mouse $IgG_2$, anti-rat $IgG_3$, anti-rat IgG, anti-rat $IgG_1$, anti-rat $IgG_2$, anti-rat $IgG_3$, anti-bovine IgM, anti-guinea pig IgG, and anti-sheep IgG; available from, e.g., Sigma, St. Louis Mo., and Gibco-BRL, Gaithersburg, Md.) or reagent to the primary antibody (e.g., fluorescein labelled biotin, rhodamine labelled biotin, fluorescein labelled strepavidin, rhodamine labelled strepavidin). In a further embodiment, the secondary antibody is labelled (e.g., fluorescent, radioactive, or enzyme labels as described above for the ubiquitin primary antibody).

In still other embodiments, ubiquitin is detected by binding to a binding molecule other than an antibody. For example, RNA and DNA molecules that bind to ubiquitin can be identified by the SELEX procedure. The basic SELEX procedure is described in U.S. Pat. Nos. 5,475,096; 5,270,163; and 5,475,096; and in PCT publications WO 97/38134, WO 98/33941 and WO 99/07724, all of which are herein incorporated by reference. The SELEX procedure allows identification of a nucleic acid molecules with unique sequences, each of which has the property of binding specifically to a desired target compound or molecule. In some particularly preferred embodiments, the binding molecule is labelled as described above.

TABLE 1

| Fluorochrome | Excitation Wavelength | Emission Wavelength |
|---|---|---|
| Hydroxycoumarin | 325 | 386 |
| Aminocoumarin | 350 | 445 |
| Methoxycoumarin | 360 | 410 |
| Cascade blue | 375; 400 | 423 |
| Lucifer yellow | 425 | 528 |
| NBD | 466 | 539 |
| R-Phycoerythrin (PE) | 480; 565 | 578 |
| PE-Cy5 | 480; 565; 650 | 670 |
| PE-Cy7 | 480; 565; 743 | 767 |
| Red 613 | 480; 565 | 613 |
| Fluorescein isothiocyanate | 495 | 519 |
| BODIPY-FI | 503 | 512 |
| Cy3 | 512; 552 | 565, 615 |
| Rhodamine isothiocyanate | 547 | 572 |
| X-Rhodamine | 570 | 576 |
| Lissamine Rhodamine B | 570 | 590 |
| PerCP | 490 | 675 |
| Texas red | 589 | 615 |
| Cy5 | 625–650 | 670 |
| Cy7 | 743 | 767 |

TABLE 1-continued

Fluorochromes

| Fluorochrome | Excitation Wavelength | Emission Wavelength |
|---|---|---|
| Allophycocyanin (APC) | 650 | 660 |
| TruRed | 490, 675 | 695 |
| APC-Cy7 | 650; 755 | 767 |

3. Methods for Quantifying Ubiquitination of Sperm

The foregoing antibodies can be used in methods known in the art relating to the localization and presence of ubiquitin, and measuring levels thereof in appropriate biological samples (e.g., semen and sperm samples). The biological samples can then be tested directly for the presence of ubiquitin using an appropriate strategy (e.g., flow cytometry, immunocytochemistry, ELISA or radioirnmunoassay) and format (e.g., microwells, dipstick, etc; See e.g., International Patent Publication WO 93/03367). Alternatively, proteins in the sample can be size separated (e.g., by polyacrylamide gel electrophoresis (PAGE), in the presence or absence of sodium dodecyl sulfate (SDS). In these size separation methods the presence of ubiquitin can be detected by methods such as immunoblotting (e.g., Western blotting)).

In some preferred embodiments of the present invention, the number of ubiquitinated sperm in a semen sample is determined by immunocytochemical techniques known in the art. In some embodiments, ubiquitinated sperm are detected in a semen sample by fixing sperm from the semen sample to a microscope slide (or in the case of electron microscopy pelleting the sample by centrifugation), labelling the sperm with a labelled (e.g., fluorescently, enzymatically, or radioactively, or colloidal gold tagged) ubiquitin antibody, and detecting the presence of the tag (e.g., by fluorescent microscopy, light microscopy, autoradiography, or electron microscopy). In other embodiments, the sperm are first bound to an unlabelled ubiquitin antibody (i.e., a primary antibody), and then the ubiquitin antibody is bound to a tagged. (e.g., fluorescently, enzymatically, or radioactively labelled) secondary antibody. A number of immunocytochemical strategies and techniques find use in the present invention. The present immunocytochemical assays can be conducted in a direct manner (e.g., the ubiquitin antibody is labelled) or indirect manner (e.g., a labelled second antibody is used to detect bound ubiquitin antibody). In some embodiments, the second antibody is conjugated to biotin or avidin so that it can be detected by a biotinylated or avidin conjugated tag. In still other embodiments, methods known in the art such as PAP (peroxidase-antiperoxidase) or APAAP (alkaline phosphatase-antialkaline phosphatase) are used to detect ubiquitin. In addition, antigen retrieval methods such as enzyme digestion and HMAR (heat mediated antigen retrieval techniques such as "microwaving" and "pressure cooking") find use in the present invention.

In some particularly preferred embodiments, the primary or secondary antibody is fluorescently tagged (e.g., with fluorescein or rhodamine) and ubiquitinated sperm are quantified by fluorescence microscopy. In some embodiments, the microscope slide is divided into a grid, the total number of sperm within the grid (e.g., a subsample) is determined via light microscopy or via fluorescent microscopy if the sperm are labelled with a DNA stain (e.g., DAPI, Molecular Probes, Eugene, Oreg.) or cytoskeleton specific stain (e.g., rhodamine-phalloidin, Molecular Probes, Eugene, Oreg.), and the number of ubiquitinated sperm observed by exciting the fluorescently tagged antibody. In other embodiments, the subsample is simply the number of sperm within a viewing field of the microscope. The percentage of ubiquitinated sperm is determined by dividing the number of sperm tagged with the labelled antibody by the total number of sperm. In some embodiments, this process is repeated for a number of subsamples (e.g., 3, 4, 5 or more subsamples) on a given slide. In other embodiments, the process is repeated for several (e.g., 2 or more) ejaculates or semen samples from an individual male. In some particularly preferred embodiments, a video image analysis system (e.g., Image 1) is utilized to count the number of sperm exhibiting a threshold level of fluorescence. In some embodiments, the test semen samples are prepared in parallel with control semen samples from a donor of known fertility. An increased amount of ubiquitinated sperm in the test semen sample is indicative of a decreased level of fertility, while approximately equal or lower levels of ubiquitination as compared to the control sample are indicative of good fertility.

In other preferred embodiments of the present invention, the level of ubiquitination in a semen sample is determined by ELISA. The present invention contemplates the use of a number of different types of ELISA formats to analyze ubiquitination in semen samples, including, but not limited to, sandwich assays, competitive assays, and direct screening assays (See e.g., Engvall, Methods in Enzymology, 70:419 [1980]; Scharpe et al., Clin. Chem. 22:733 [1976]; Schuurs et al., Immunoassay 1:229 (1980); Wisdom, Clin. Chem. 22:1243 [1976]).

In some preferred embodiments, a test semen sample is diluted (e.g., from about $3 \times 10^7$ sperm per ml to about $1 \times 10^4$ sperm per ml) and an aliquot (e.g., about 1 to 50 $\mu$l) added to a well in ELISA assay plate (e.g., a Corning-Costar 96 well plate). The samples are washed and then a ubiquitin antibody is added and allowed to bind. In some embodiments, the ubiquitin antibody is tagged with an enzymatic label (e.g., alkaline phosphatase or horseradish peroxidase). In other embodiments, an enzymatically tagged second antibody is used to detect the bound ubiquitin antibody. In some particularly preferred embodiments, the second antibody is conjugated to alkaline phosphatase. In some embodiments, the presence of alkaline phosphatase is detected by adding alkaline phosphatase substrate (Zymed, So. San Francisco, Calif.) to the well, incubating, and reading the results at 405 nm in a photocolorimeter, plate reader, or spectrophotometer. In some embodiments, control semen samples from donors of known fertility are included and analyzed in parallel with the test semen samples. An increased amount of ubiquitinated sperm in the test semen sample as assayed by an increase in the signal utilized in the ELISA is indicative of a decreased fertility, while approximately equal or lower levels of ubiquitination as compared to the control sample are indicative of good fertility.

In still other preferred embodiments of the present invention, the level of ubiquitination in a semen sample is determined by flow cytometry. Flow cytometry generally involves the use of a fluid stream containing cells (e.g., sperm) that is passed through a beam of light, usually generated by a laser (e.g., argon, helium-neon, krypton, or dye laser), so that one cell at a time passes through the light path. The photons of light, which are scattered and emitted by the cells following their interaction with the laser beam, are separated into constituent wavelengths by a series of filters and mirrors. The separated light falls on a detector to generate an analog signal, this signal is then converted to a digital signal, which is accumulated and displayed in frequency distribution (i.e., histogram). The resulting value obtained is proportional to the amount of light emitted from each individual cell (See e.g., McCoy, *Flow Cytometry and Clinical Diagnosis*, Karen et al., eds., ASCP Press, Chicago, p. 26–55 [1994]; *Flow Cytometry: A Practical Approach*, Ormerod, ed., IRL Press, Oxford [1994]; *Handbook of Flow Cytometry Methods*, Robinson ed., Wiley-Liss, New York, 1993).

In some embodiments, the sperm from a semen sample are treated (e.g., with formaldehyde) and incubated with a primary ubiquitin antibody (e.g., KM 693 or MK-12-3). The sperm-primary antibody complexes are then incubated with fluorescently tagged second antibody (e.g., FITC conjugated goat anti-mouse IgM or IgG). The labelled sperm are then analyzed via flow cytometry. In some preferred embodiments, at least one control sample from a donor of known fertility is analyzed in parallel with test semen samples. In some embodiments, the data are analyzed by plotting the relative fluorescence for each sample and recording the median value. The median value provides the percentage of cells with average fluorescence and is increased proportionally to the increase in the number of labelled cells (i.e., the median value is the percent of sperm with average specific fluorescence). An increase in the median value of the test semen sample is correlated with an increase in ubiquitination and is indicative of a decreased level of fertility. In contrast, lower levels of ubiquitination (i.e., indicated by a lower median value) as compared to the control sample are indicative of good fertility.

In other embodiments of the present invention, fertility is assessed by combining ubiquitination analysis with traditional semen quality analysis parameters, including, but not limited to, ejaculate volume, sperm count, sperm motility, forward progression, sperm morphology, pH, agglutination, leukospermia, and viscosity. In infertile couples, the pregnancy history, fertilization, and cleavage rates after in vitro fertilization may be combined with some or all of the above parameters.

4. Fertility Assay Kits

In some embodiments of the present invention, kits are provided that contain reagents for performing the assays described above. In some embodiments, the kits include a container of ubiquitin antibody. In further embodiments, the kits include a container of semen sample from a donor of known fertility. In some embodiments where the primary antibody is not labelled, the kit further include a container of a labelled second antibody. In some preferred embodiments, the kit also includes directions for performing the ubiquitin assays described above and in the Experimental section below. The directions include methods for preparing the semen sample, fixing the sperm, binding the primary ubiquitin antibody to the sperm, labelling the primary antibody-sperm complex with a labelled second antibody, and detecting the complex via flow cytometry, ELISA, or immunocytochemistry. The kit instructions also provide methods for quantifying the results and comparing the results obtained for test samples to results obtained for the control samples, and for correlating these results with fertility.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); $\mu$M (micromolar); mol (moles); mmol (millimoles); $\mu$mol (micromoles); nmol (nanomoles); pmol (picomoles); g (grams); mg (milligrams); $\mu$g (micrograms); min. (minute); ng (nanograms); l or L (liters); ml (milliliters); $\mu$l (microliters); cm (centimeters); mm (millimeters); $\mu$m (micrometers); nm (nanometers); ° C. (degrees Centigrade); and, Sigma (Sigma Chemical Co., St. Louis, Mo.); Kamyia (Kamyia Biomedical Comp., Seattle, Wash.), Molecular Probes (Molecular Probes, Eugene, Oreg.); Dynal (Dynal, Lake Success, N.Y.); Costar (Costar, Coming, N.Y.); ABS (ABS Inc., De Forest, Wis.), Follas (Follas Laboratories, Indianapolis, Ind.); Vector (Vector Laboratories, Burlingame, Calif.); FITC (fluoroscein isothiocyanate); TRITC (rhodamine isothiocyanate).

EXAMPLE 1

Identification of Ubiquitinated Sperm

This example demonstrates the presence of ubiquitinated sperm in the ejaculates of several species. Ubiquitinated sperm were detected by immunofluorescence, colloidal gold labelling, and Western blotting.

Antibodies and Probes. Bovine data including domestic bulls, gaur and buffalo, were obtained using mouse monoclonal antibody MK-12-3 (MBL, Nagoya, Japan), raised against the purified bovine erythrocyte ubiquitin. Antibody Ab 1690 against bovine erythrocyte ubiquitin was used as a control in some tests. Human and rhesus data were obtained using mouse monoclonal antibody KM 693 (Kamyia). Rhodamine-phalloidin (actin stain) and DAPI (DNA satin) were purchased from Molecular Probes.

Sperm isolation. Ejaculated bull sperm were purchased as frozen straws from American Breeders Services (De Forest, Wis.) and, where mentioned, separated on a two-layer percoll gradient (Parrish et al., Theriogenology 25:591–600 [1986]). Epididymal and testicular sperm were obtained by mincing of the appropriate tissue purchased from a local slaughterhouse. Cell suspensions were washed in SpermTL medium and used as described below.

Human sperm were obtained from 17 consenting infertility patients (#1–17) currently participating in the treatment program at the Tohoku University Hospital, Sendai, Japan. Samples were coded so that researchers could not reveal the identity of patients and frozen in liquid nitrogen. Appropriate protocols approved by both Tohoku University and Oregon Health Sciences University were strictly followed. Samples from fertile donors (#1084 and 1127) were purchased from Follas Laboratories. Frozen ejaculates were thawed in warm water and washed by centrifugation through Sperm TL medium supplemented with HEPES.

Rhesus sperm were obtained by masturbation from trained rhesus monkey males from the colony at the Oregon Regional Primate Research Center, Beaverton, Oreg. Gaur and buffalo sperm samples were obtained from bulls housed at the Henry Doorly Zoo, Omaha, Nebr., and kindly donated by Henry Doorly's Reproductive Sciences Division. Mouse sperm were obtained from male Balb/c mice by the extraction of epididymal tissue.and release of the sperm into culture medium.

Ubi-Beads. Uncoated (4.5 $\mu$m diameter) and Tosyl-activated (2.8 $\mu$m) magnetic beads were purchased from Dynal, and coated using Dynal MPC device according to manufacturers recommendations with the purified bovine erythrocyte ubiquitin (Sigma) in PBS (pH 7.3) at the concentration of 150 $\mu$g/ml. Beads were incubated with ubiquitin overnight at 37° C. in a shaking waterbath, washed and stored at 4° C. until used.

Tissue Isolation and Epididymal Cell Culture. Pieces of caput, corpus, and cauda epididymal tissue (5×5×5 mm) were transferred into TL-HEPES (Parrish et al., Theriogenology 25:591–600 [1986]) medium and digested using techniques adapted from Moore et al., (Fertil. Steril. 58, 776–783 [1992]) and Cooper et al., (Cell Tissue Res. 256, 567–572 [1989]). A first digestion (30 min. at 37° C., with shaking) was done in 2 mg/ml collagenase II (Sigma) in TL-Hepes containing 3 mg/ml BSA-fraction V, 0.2 mM pyruvate and 0.5 μl/ml gentamicin. A second digestion (20 min. at 37° C., with shaking) was in TL-HEPES with above supplements, 2 mg/ml collagenase II, 2 mg/ml hyaluronidase and 0.33 mg/ml elastase (all from Sigma). Isolates cells and tissue fragments were collected by centrifugation, washed in TL-HEPES and plated onto 6-well culture clusters (Costar) in DMEM medium (Gibco-BRL) supplemented with 10% fetal calf serum, 50 U/ml penicillin, 50 μg/ml streptomycin, 1 mM pyruvate, 0.1 μM water soluble testosterone and 1 μM dihydrotestosterone (all from Sigma). Cultures were maintained for up to 15 days with medium exchange every two days. Ubiquitin coated Dynabeads were added to cultures in a final concentration of 10,000 beads/ml (50,000 per well) or as otherwise specified.

Immunofluorescence. Two microliters of sperm. pellets from eachmale were resuspended in 500 μl drops of 37° C. warm KMT medium on poly-L-lysinecoated microscopy coverslips (22×22 mm) on a warm plate and allowed to attach for 5 min. Coverslips were submerged in 2% formaldehyde in PBS and fixed for 40 min. No permeabilization was performed. Samples were then blocked for 25 min. in 5% normal goat serum (NGS) in PBS and incubated for 40 min with the monoclonal antibody KM 693 raised against the recombinant human ubiquitin (Kamyia; dil. ¹⁄₁₀₀). PBS with 1% NGS was used for washing and dilution of primary and secondary antibodies. After washing, samples were incubated for 40 min with TRITC-conjugated goat anti-mouse IgM (Zymed; dil. ¹⁄₈₀) and DNA-stain DAPI (Molecular Probes, Eugene, OR) was added to this solution 10 min before the end of incubation. Samples were washed and mounted on microscopy slides in Vectashield (Vector) medium. Detection of perinuclear theca proteins and acrosin in patient #1 was performed as described previously (Sutovsky et al., Human Reprod., 14: 2301–2312 [1999]). Samples were examined using a Zeiss Axiophot microscope. Images were captured by a Princeton Digital camera using MetaMorph software, edited by Adobe Photoshop 4.0 and printed by SONY UP-D 8800 dye sublimation printer.

Electron Microscopy and Colloidal Gold Immunocytochemistry. Sperm samples for electron microscopy were treated using centrifugation/resuspension cycles instead of being attached to glass coverslips. Resulting sperm pellets were processed with anti-ubiquitin antibodies as described for immunofluorescence, except that the fluorescent conjugated secondary antibodies were replaced with goat-anti-mouse IgG/IgM conjugated with 10 nm colloidal gold. Both colloidal gold-labelled samples and those of fresh sperm/epididymal cells were then fixed in a mixture of 2% paraformaldehyde and 0.6% glutaraldehyde. in cacodylate buffer, post-fixed in 1% osmium tetroxide, dehydrated by an ascending ethanol series (30–100%) and embedded in PolyBed 812 resin. Ultrathin sections were cut on a Sorval MT2B ultramicrotome, placed on 100 MESH copper grids and stained in two steps with uranyl acetate and lead citrate. Serial sections were examined and photographed in a Phillips EX 120 STEM electron microscope. Negatives were scanned by an Umax Magic Scan flat bed scanner, recorded on Jazz disc, and printed on a Sony UPD 8800 videoprinter using Adobe Photoshop 4.0 editing software.

Western Blotting. Sperm were lysed in 0.5 ml of a sample buffer (1 M NaCl, 20 mM imidazole, 1 mM EDTA, 5 mM benzamidine HCl, 5 mg/ml leupeptin and 1 mg/ml pepstatin A, pH 6.0), run on a 10% SDS-PAGE under non-reducing or reducing and denaturant conditions, transferred to Hybond™ sheets, using a dry system, at 0.8 mA per cm2, blocked with 2% PBS-BSA for 1 hr, incubated overnight at 4° C. with the mouse monoclonal antibody MK-12-3 against bovine erythrocyte ubiquitin (MBL; dil. ¹⁄₂₀₀), washed and incubated with goat anti-mouse IgG/Horseradish peroxidase (Sigma; dil. ¹⁄₂₀₀₀). The bands were developed using the ECLplus™ system (Amersham) following the manufacturer's directions. Protein was determined by Pierce bicinchoninic acid method (Pierce) according to the manufacturer's specifications.

Ubiquitinated spermatozoa were detected in the sperm samples from breeding domestic bulls (*Bos taurus*) by immunofluorescence labelling with monoclonal antibody MK 12-3 (generated against purified bovine erythrocyte ubiquitin). The ubiquitinated sperm cells displayed visible defects of the sperm head and/or axoneme, and ubiquitinated twin sperm and sperm with two tails/heads were frequently seen. Ultrstructural analysis suggested that these sperm cells were ubiquitinated mainly on their surface, a presumption later confirmed by Western blot analysis and by the labeling of sperm in the absence of permeabilization. In addition to domestic bull sperm, ubiquitin was detected by MK-12-3 in defective spermatozoa of Asian wild cattle, gaur (*Bos gaurus*), and American buffalo (*Bos bison*). Similarly, the antibody KM-693 raised against recombinant human ubiquitin revealed the ubiquitination of defective sperm samples from rhesus monkey (*Macaca mullata*) males and in men. As with the domestic bulls tested, the ubiquitinated sperm cells of all other species were visibly abnormal. In line with these data, ubiquitin was previously detected in human epididymal cells (Fraile et al., Biol. Reprod. 55:291–297 [1996]) and seminal plasma (Lippert et al., J. Androl. 14, 130–131 [1993]), though no connection has been made to sperm resorption, selection or fertility.

The abnormal spermatozoa in the ejaculates of domestic bulls were primarily surface ubiquitinated. To further investigate the distribution of the ubiquitinated areas in the sperm, Western blot analysis was performed on the live and motile, and dead and immotile sperm fractions obtained by Percoll separation. These fractions were analyzed either under reducing, or under non-reducing conditions. No ubiquitinated bands were detected in the live sperm fraction probed under non reducing conditions, whereas the ubiquitinated substrates were abundant in the dead sperm fraction, even in the absence of reducing agent DTT. Both live and dead sperm displayed a set of ubiquitinated bands after DTT treatment exposing the disulfide bond-stabilized sperm proteins that probably become constitutively ubiquitinated during spermatogenesis. The relative abundance of ubiquitinated sperm in live and dead sperm fractions were analyzed by immuno fluorescence with MK-12-3. Experiments with an unrelated antibody against bovine erythrocyte ubiquitin, Ab1690, also resulted in staining of abnormal sperm. The inaccessibility of ubiquitinated epitopes in live sperm can be explained by the presence of intrinsic ubiquitinated substrates in the mature sperm, carried over from the final steps of spermnatogenesis. For example, sperm mitochondria become ubiquitinated during mammalian spermatogenesis, and the ubiquitin is masked by disulfide bond-crosslinking during epididymal passage. Similarly, histones, and possibly other sperm head substrates are ubiquitinated during spermatogenesis and can only be detected after disulfide bond reduction. Therefore, it appears that the abnormal spermatozoa become strongly ubiquitinated on their surface during epididymal passage, while the live sperm carry only basal amounts of surface-bound ubiquitin.

EXAMPLE 2

Site of Sperm Ubiquitination

In this Example, the site of the ubiquitination of defective sperm was determined by comparing the percentage of ubiquitinated sperm in individual compartments of the genital tract of two different bulls. Unless otherwise indicated, the experimental procedures are as described in Example 1. One thousand sperm from each bull were randomly examined after immunostaining with MK 12-3 in two replicates (total of 2000 sperm/bull). Although no surface-ubiquitinated spermatozoa were found in the testicular rete, the total rate of ubiquitinated sperm rose to 5.3% in bull #1 an 5.2% in bull #2, and then decreased to 0.8% and 0.9%, respectively in cauda epididymis, with the values from corpus epididymal samples being approximately 55–70% of those in caput. The types of defects and ubiquitination patterns found in the epididymal sperm were similar to these seen in the ejaculated sperm.

Immunostaining of paraffin tissue sections revealed massive accumulation of ubiquitin in caput epididymis, mainly localized in the basal compartment of elongated epididymal epithelial cells (EEC) and in the tips of the microvilli lining the lumen of epididymal tubules. Interstitial cells were also strongly stained. The microvillar localization of ubiquitin in EEC may correspondwith the apocrine secretion of ubiquitin into the lumen of epididymal ductuli, as many other epididymal proteins are known to be secreted in this manner. Typically, such proteins are enclosed in the secretory bodies detaching from the apical protrusions of epididymal cells. Sperm cells with coiled, ubiquitinated tails were occasionally detected on the sections. Most sperm cells in the lumen of caput epididymal ductuli also had ubiquitinated cytoplasmic droplets, and the ubiquitinated structures of identical size and shape were often found lining the surface of epididymal epithelium. These residual cytoplasmic droplets with high enzymatic activity appear to be a carryover from testis. There may be specific mechanism for their removal/resorption during epididymal passage (Hermo et al., Am. J. Anat. 183:107–124 [1988]). The distribution of ubiquitin in the corpus epididymis was similar to that of the caput, whereas the epithelial cells were shorter, the wall of the epididymal tubules was thinner, and the apical ubiquitin staining was less intense in the cauda epididymis. Somatic cells (perhaps the resident macrophages) mixed with sperm were sometimes found in the lumen of cauda epididymal tubules. Sperm in rete testis were not ubiquitinated, though there was some ubiquitin accumulation in the cells of afferent ductuli. No distinct ubiquitination of abnormal sperm was found in the seminiferous tubules adjacent to the rete and secondary antibody binding was not detected after the omission of primary antibody in negative controls of caput epididymnal sections.

Ultrastructural analysis revealed the presence of disintegrating sperm tails and heads deep in the cytoplasm of EEC and numerous sperm with abnormal configurations of perinuclear cytoskeleton and axoneme were found attached to, or embedded in the apical cytoplasm of EEC in the caput epididymis. Cytoplasmic droplets filled with membrane vesicles were frequently found on the midpiece of caput epididymal sperm, or shed into the lumen of epididymal ductuli. Most sperm in the cauda were normal, though some defective sperm were also found in this compartment. Colloidal gold labelling with MK-12-3 revealed strong ubiquitination of cytoplasmic droplets, as well as the secretion of ubiquitin by EEC in the formn of secretory bodies and vesicles. Such ubiquitin-containing particles were often attached to sperm heads and/or tails in caput epididymis.

These data demonstrate that the ubiquitination of defective spermatozoa occurs mainly. in the proximal epididymal compartment, caput epididym is, and that most of the ubiquitinated sperm (approx. 80–85%) are resorbed by epididymal epithelium. Similarly, the residual cytoplasmic droplets are ubiquitinated and resorbed during epididymal passage. Paradoxically, the number of ubiquitinated defective sperm seems to be lower in the cauda epididymis than in the ejaculate (Table 1). A similar paradox was observed in the sperm of domestic cat (Axnér et al., J. Androl. 20:415–429 [1998]) and could be attributed to the fact that a significant portioin of the ejaculated sperm may be extruded from the caput and corpus epididymis before the processing of defective sperm can be completed.

EXAMPLE 3

Ubiquitin-Dependent Sperm Internalization

This example describes an in vitro system for studying ubiquitin-dependent sperm internalization. This in vitro system to study epididymal sperm ubiquitination was developed using EEC isolated by enzymatic digestion of epididymal tissue. Individual cells as well as aggregates of elongated EEC were obtained and plated in six well culture dishes containing medium with serum and testosterone (see Example 1 for procedures). Concomitantly, 4.5 $\mu$m or 2.8 $\mu$m magnetic spheres were coated with purified bovine erythrocyte ubiquitin (ubi-beads). Both isolated cells and ubi-beads crossreacted with MK-12-3, whereas no crossreactivity was seen in uncoated control beads. The isolated cell suspensions also contained the digested sperm that did not crossreact with MK-12-3. On day 2–3 of culture, the cells plated on the bottom of culture dishes and coated ubi-beads were added to the culture in final concentration of 150,000 beads/well. On day 3–4, the EEC formed large epithelial plaques, often containing attached beads. Sperm introduced into culture with isolated EEC became strongly ubiquitinated. Some of the plaques already contained the internalized ubi-beads and sperm at this point. The assembly of microfilament bundles was seen around the internalized beads and was probably involved with their internalization. At day 10 of culture (i.e., day 9 of co-culture with ubi-beads), the epithelial plaques engulfed most of the beads, often forming large clusters of beads that also contained internalized sperm. Such plaques still produced ubiquitin and actively assembled actin microfilaments, as documented by double labelling with MK-12-3 and rhodamine-phalloidin. A quantitative study (Table II) demonstrated that the ubiquitin-coated beads have a substantially higher affinity to epididymal epithelial cells than the beads coated with control protein (BSA-V) or uncoated beads.

Ultrastructural studies confirmed that the cells containing endocytosed sperm also internalized the ubi-beads. Sperm at various stages of disintegration were found next to the ubi-beads in the cytoplasm of such cells. Large lysosomal vesicles were regularly found next to the internalized ubi-beads and sperm, sometimes engulfing the whole sperm nuclei. Although the freshly coated sperm displayed strong labelling when processed with MK-12-3/colloidal gold, this was diminished in the internalized beads at day 3 and almost completely disappeared from the internalized beads at day 10, while the cells containing such beads displayed strong cortical/surface labelling. It is possible that ubiquitin was removed from the internalized beads in a manner similar to the endocytosis and recycling of SGP-2 antigen in the cauda epididymis (Adonian and Hermo, J. Androl. 20:415–429 [1999]; Igdoura et al., Microsc. Res. Tech. 29:468–480 [1994]). This ubiquitin may then be recycled and transported towards the surface of EEC for secretion. Similar to ubi-beads, the internalized sperm did not display detectable ubiquitin labelling at day 10, even though ubiquitin was detected on adjacent lysosomes and in the surrounding cytoplasm. In contrast, most EEC displayed strong surface labelling and secretory bodies similar to those found in situ. The endocytosis of ubi-beads and dead sperm introduced into the co-culture with isolated EEC demonstrates that these cells continue secretion od ubiquitin and sperm endocytosis even after being isolated and plated onto culture dishes. The role of ubiquitin as a possible specific receptor for the endocytosis of defective sperm may provide a basis for the design of male contraceptives based on ubiquitin epitopes.

It is not intended that the present invention be limited to particular mechanism of action. Indeed, an understanding of the mechanism is not necessary to make and use the present invention. However, these data demonstrate that defective mammalian spermatozoa undergo surface ubiquitination during epididymal passage, making them prone to resorption and thereby eliminating them from the pool of sperm capable of fertilizing an egg. Although it is likely that the defective spermatozoa are ubiquitinated because of their structural damage, the questions of how such sperm are recognized by the ubiquitination machinery and how they are disposed of by endocytosis remain to be answered. One possible explanation is that the epididymal ubiquitination is the common end-point of apoptotic mechanisms operating in the testis. Such a mechanism may recognize the structural damage of sperm DNA (Sakkas et al., Exp. Cell Res. 251:350–355 [1999]) and/or accessory structures. In addition, cell surface proteins, such as apoptotic Fas-ligand on the surface of defective human sperm (Sakkas et al., Exp. Cell Res. 251:350–355 [1999]), could be a signal for the ubiquitination of such sperm cells. It is indeed very intriguing that Sakkas et al. found an elevated percentage of Fas-positive sperm in ejaculates of infertility patients. However, ubiquitin and Fas, do not co-localize. Furthermore, Fas, in contrast to ubiquitin, is not found in the ubiquitinated cytoplasmic droplets and somatic/spermatogenic cells present in the ejaculates of infertility patients. An alternative, or perhaps upstream-of-Fas-apoptotic signal for the ubiquitination of defective sperm may be the Blc-2 controlled release of cytochrome-c from sperm mitochondria, which in somatic cells triggers the apoptotic pathway. Besides providing the apoptotic signal, this event also alters the structure of the inner and outer layers of the mitochondrial membrane where cytochrome-c is sandwiched. This membrane disruption exposes the proteins of the inner mitochondrial membrane. An unexpected, high molecular weight isoform of prohibitin, a conservative, 30 kDa protein of the inner mitochondrial membrane, has been identified in bull sperm, where it appears to be ubiquitinated and masked by the disulfide bond cross-linking of the mitochondrial sheath. Such ubiquitinated prohibitin could be exposed by mitochondrial membrane rupture in the apoptotic, dead sperm and targeted for polyubiquitination by the epididymal machinery. In accordance with this possibility, ubiquitination of the mitochondrial sheet has been observed in some dead sperm with no apparent structural abnormalities.

Yet another pathway leading to the ubiquitination of defective sperm could be through the misfolding or denaturation of sperm surface antigens. The amino acid sequence of the N-terminal domain determines the half-life of proteins and is subject to ubiquitination when the tertiary structure of such proteins is altered (N-end rule pathway; Varshasky, Genes Cells 2: 13–28 [1997]). This domain could be the signal for surface ubiquitination in defective sperm. A number of other sequence motifs and signals, including hydrophobic protein surface domains, phosphorylation and a variety of destruction motifs also serve for substrate targeting in the ubiquitin system.

Ubiquitination has previously been implicated in a number of endocytotic events, including the endocytosis of membrane receptors and plasma membrane-anchored transporters. The present invention shows for the first time that a whole sperm cell can be surface-ubiquitinated and endocytosed. Similar to the proteolysis of endocytosed receptors, the destruction of the endocytosed sperm seems to occur mainly by the means of lysosomal proteolysis.

EXAMPLE 4

Correlation of Sperm Ubiquitination to Fertility

This example demonstrates the correlation of sperm ubiquitination to fertility in a group of bulls of varied fertility. These data indicate that the cellular proteolytic marker ubiquitin is conjugated to defective spermatozoa during epididymal passage. Such defective spermatozoa include those that can be detected by electron microscopy or immunocytochemistry (e.g., small nuclear vacuoles and abnormal/missing microtubule doublets). Sperm obtained from ABS, were analyzed by immunocytochemistry with MK-12-3 detected with FITC-conjugated secondary antibodies (FITC-anti-mouse IgG). One sperm straw from each bull was thawed in each of three experiments and processed for immunnofluoresence as described in Example 1. One thousand sperm were counted and evaluated for the presence or absence of ubiquitin labelling in 8 to 10 viewing fields of an epifluoresence microscope at 63x. Among these bulls, Bull 4 was rated by the semen supplier as above average, Bulls 1 and 2 were rated as average, and bulls 3 and 5 were rated as average to low in fertility parameters (non-return rate). As can be seen in Table 2, the percent ubiquitination correlates to the fertility ratings of the semen supplier. It was not necessary to distinguish between weak labelling and strong labelling in the bull sperm samples. The specific labelling of damaged bull sperm is very strong and there is little variability and little background staining. This allows division of the processed sperm into "positive" and "negative" labelled groups. This is in contrast to human sperm where even normal sperm bear a certain degree of ubiquitination and methods such as flow cytometry or ELISA are used to determine the total amount of ubiquitin in a sample (see below).

These results indicate that the ubiquitination assays of the present invention provide an unambiguous semen quality assay with the ability to predict the reliability of artificial insemination without costly and lengthy research. Morphological semen analysis based on the number of grossly mis-shaped, damaged sperm have certain predictive value with regard to a bull's reproductive performance, yet it is limited by the fact that many abnormalities are often missed at this examination level, and the fact that other abnormalities can be introduced through handling (e.g., washing, pipetting, and centrifuging). The major advantages of the methods of the present invention over conventional sperm quality analyses include the advantage that anomalies introduced by sample processing do not bias the results and that sperm that are damaged but otherwise appear normal are identified by the assay.

TABLE 2

Correlation of Sperm Ubiquitination to Fertility

| Bull | 1 | 2 | 3 | 4 | 5 |
|---|---|---|---|---|---|
| Supplier fertility rating | Average | Average | Average to low | Above average | Average to low |
| % Ubiquitination Replicate 1 | 3.9 | 5.3 | 4.7 | 1.5 | 5.3 |
| % Ubiquitination Replicate 2 | 3.7 | 3.3 | 4.3 | 1.7 | 4.5 |
| % Ubiquitination Replicate 3 | 3.9 | 3.8 | 4.6 | 1.3 | 4.7 |
| Average % Ubiquitination All replicates | 3.83 | 4.13 | 4.53 | 1.50 | 4.83 |

EXAMPLE 5

Correlation of Sperm Ubiquitination to Fertility

This example demonstrates the correlation of sperm ubiquitination to fertility in a different group of bulls of varied fertility. Sperm obtained from ABS, were analyzed by immunocytochemistry with FITC conjugated MK-12-3 immunocytochemistry with MK-12-3 detected using FITC-conjugated secondary antibodies (FITC-anti-mouse IgG). One sperm straw from each bull was thawed in each of two experiments and processed for imm unofluorescence as described in Example 1. One thousand sperm were counted and evaluated for the presence or absence of ubiquitin labelling in 8 to 10 viewing fields of an epifluorescence microscope at 63x. The bulls were rated for fertility by the supplier as described in Example 4. The samples from bulls 4 and 6 were not ranked for ubiquitination as the results were apparently confounded because initial ejaculates were discarded because of poor fertility and samples retaken shortly thereafter. It is believed that this was caused by the fact that samples taken shortly after the first ejaculation had not remained in the epididymis for a sufficient time to be ubiquitinated. As can be seen in Table 3, the percent ubiquitination correlates to the fertility ratings of the semen supplier.

EXAMPLE 6

Correlation of Sperm Ubiquitination to Fertility

This example demonstrates the correlation between sperm ubiquitination and fertility in human subjects. Ubiquitination was assayed by ELISA, flow cytometry, and immunofluorescence as indicated.

Sperm samples. Ejaculates were obtained from 17 consenting infertility patients (#1–17) participating in the treatment program at the University Hospital, Sendai, Japan. Samples were coded so that researchers could not reveal the identity of patients and relevant guidelines of the NIH and Japanese Ministry of Health were strictly followed. Samples from fertile donors (#1084 and 1127) were purchased from Follas Laboratories. Frozen ejaculates were thawed in warm water and washed by centrifugation through Sperm TL medium supplemented with HEPES.

Immunofluorescence. Two microliters of sperm pellets from each man were resuspended in a 500 $\mu$l drops of warm (37° C.) KMT medium on poly-L-lysine coated microscope coverslips (22×22 mm) on a warm plate and allowed to attach for 5 min. Coverslips were submerged in 2% formaldehyde in PBS and fixed for 40 min. No permeabilization was performed. Samples were then blocked for 25 min. in 5% normal goat serum (NGS) in PBS and incubated for 40 min with the monoclonal antibody KM 693 raised against the recombinant human ubiquitin (Kamyia; dil. 1/100). PBS with 1% NGS was used for washing and dilution of primary and secondary antibodies. After wash, samples were incubated for 40 min with TRITC—conjugated goat anti-mouse IgM (Zyrmed; dil. 1/80) and DNA-stain DAPI (Molecular Probes) was added to this solution 10 min before the end of incubation. Samples were washed and mounted on microscope slides in Vectashield (Vector) medium. Samples were examined in Zeiss Axiophot microscope, images were captured by a Princeton Digital camera using MetaMorph software, edited by Adobe Phottoshop 4.0, and printed using a SONY UP-D 8800 dye sublimation printer.

Flow Cytometry. Sperm were fixed in a suspension of 2% formaldehyde in PBS, blocked and incubated with primary antibody as described for immunofluorescence, then incubated with FITC-conjugated goat anti-mouse IgM (Zymed; dil. 1/80), washed and resuspended in 500 $\mu$l of pure PBS without serum. Blank samples were prepared for each

TABLE 3

Correlation of Sperm Ubiquitination with Fertility

| Bull | 1 | 2 | 3 | 4 | 5 | 6 |
|---|---|---|---|---|---|---|
| Supplier fertility rating | Excellent | Average | Above average | Low | Average | Low |
| % Ubiquitination Replicate 1 | 2.6 | 5.1 | 3.8 | 1.9 | 5.1 | 1.7 |
| % Ubiquitination Replicate 2 | 4.5 | 3.9 | 4.0 | 1.2 | 5.9 | 2.0 |
| Average % ubiquitination | 3.55 ± 1.34 | 4.50 ± 0.84 | 3.90 ± 0.14 | 1.55 ± 0.49 | 5.50 ± 0.57 | 1.85 ± 0.21 |
| Relative ranking based on % ubiquitination | 1 | 3 | 2 | — | 4 | — | experimental sample by omitting the primary antibody. Typically, samples from five infertility patients and one fertile donor were prepared and analyzed per session. Samples were measured using Becton Dickinson's FACS Calibur Analyzer at 488 nm. A sample of PBS buffer used for labelling was used to eliminate non-specific fluorescence contributed by processing solutions and a blank sperm sample, processed with secondary antibody alone, for each corresponding patient/donor was run before each of the anti-ubiquitin-labelled samples. Five thousand cells were measured for each sample in each analysis. The relative fluorescence (no units) was plotted separately for each sample and the median value was recorded. This median indicates the % of cells with average fluorescence and increased proportionally to the increase in the number of labelled cells. After each run, leftover samples were stored overnight at 4° C. and reevaluated the next day. No significant differences were found between such reruns of the original results.

ELISA assays. Sperm concentration was determined by hemocytometer for each thawed sperm sample and then the sperm were. diluted to 22 million/ml and serial dilutions of 2.2, 0.22 and 0.022 million sperm/ml were prepared in PBS with 0.05% Tween 20 (PBS-T; Sigma). Two hundred microliters of diluted sperm were loaded onto 96-well ELISA plates (Corning-Costar) and sequentially incubated on the plates overnight at 4° C. without any additives, with 1% BSA for 30 min. at room temperature (RT), with anti-ubiquitin antibody KM693 (dil., $1/200$ in PBS-T) for 2 hours at RT, washed 3× with PBS-T, incubated with alkaline phosphatase-conjugated goat anti-mouse IgM (Zymed, dil. $1/1000$) for 2 h at RT, washed 3× in PBS-T, incubated with 200 µl of alkaline phosphatase-substrate (Zymed) for 30 min and read at 405 nm wavelength in a photocolorimeter, plate reader, or spectrophotometer.

The sperm of two fertile donors (males #1084 and 1127) and 17 infertility patients (#1 through #17) were assayed by immunofluorescence (all men), flow cytometry (all men except donor #1084) and ELISA (donor #1127, patients #3, 4, 6, 8, 9, 13 and 14) using antibodies against the recombinant human ubiquitin (KM 693) and appropriate conjugates of secondary antibodies.

By immunofluorescence, the sperm of fertile donors displayed a typical ovoid shape of the sperm head and a straight sperm tail with a mitochondrial sheath of even diameter. Weak ubiquitin labelling was found on the surface of the sperm tail's principal and end pieces in most sperm, and, in some cases, on the equatorial segment of the sperm head. No permeabilization was used in these experiments in order to avoid the contribution of constitutively ubiquitinated sperm substrates to the fluorescent signal. Abnormal sperm with strongly ubiquitinated, coiled or lasso tails were occasionally found in the sperm from both fertile donors. Donor #1127 was used as a standard sample for flow cytometry, where his median value (% of sperm with average specific fluorescence) reached 22.88% in a first experiment and 18.43% in a second experiment.

Patient #1 had a high proportion of ubiquitinated, round-headed sperm typical of globozoospermy, a rare spermatogenic fertility disorder arising from the failures of sperm nuclear condensation and aberrant differentiation of perinuclear cytoskeleton. This diagnosis was also supported by the absence or malformations of acrosome and perinuclear theca in this sample. Other abnormalities included lasso tails and round and elongated spermatids present in the ejaculate. This case was previously diagnosed as male infertility, which is unambiguously supported by ubiquitin data. No fertilization, cleavage or pregnancy was obtained, sperm count and motility were low (18.3 million/ml and 20%, respectively).

Although patient #2's sample contained mostly normal sperm, malformations of the sperm heads were observed. Accordingly, the infertility diagnoses for this couple was tubal, with no pregnancy but excellent fertilization and cleavage rates (both 83.3%) and sperm characteristics (136.3 million/ml; 88.3%).

Patient #3 displayed significantly higher median (40.68% vs. 22.88% in #1127) and a shift in the distribution of highly fluorescent cells by flow cytometry. By immunofluorescence, the major defect revealed was sperm with swollen heads and lasso tails. Heads separated from tails, nuclear vacuoles and cytoplasmic droplets were also frequent. Infertility was deemed idiopathic with good sperm motility (88.3%). Primary sterility was indicated in this patient and no pregnancy was obtained. Thus, the present ubiquitin assays provide a clear diagnosis of male factor infertility in this previously unexplained case.

For patient #4, the major defect in his sample was large amounts of residual cytoplasm in the form of irregularly shaped clusters, although most sperm were morphologically normal. Flow cytometry median was 27.38% (as opposed to 22.88% in #1127), and a significant shift in fluorescence distribution was observed. Both tubal and male factor infertility were previously diagnosed, with low sperm count (34 million/ml) and motility (23.7%), although a pregnancy was obtained. Male factor infertility was confirmed by ubiquitin assays.

The major defect in the sample from patient #5 was the presence in the ejaculate of residual cytoplasmic bodies, normally removed by Sertoli cells in the testis. Nuclear vacuoles and swollen sperm heads were also frequent. Flow cytometry median was 28.39% as compared to 18.43% in #1127. Sterility was previously diagnosed as female factor, tubal, with average sperm count of 61.7 million/ml and motility of 59.9%. No pregnancy was obtained despite of the treatment for tubal infertility. However, the presence of residual, ubiquitinated cytoplasm suggest the contribution of previously undiagnosed male factor infertility in this case. Thus, again, the present ubiquitin assays provide a clear diagnosis of male factor infertility in this previously unexplained case.

The prevailing abnormality in the sample from patient #6 was the presence in the ejaculate of small cells with nuclei, probably leukocytes or immature spermatogenic cells. Swollen sperm heads were also frequent. Flow cytometry median was 29.43% (compared with 22.88% in #1127). Sperm count was high (256 million/ml), while only 25% of sperm were motile and previous diagnosis was male factor infertility. Pregnancy was obtained. Ubiquitin data support male factor infertility diagnosed previously.

The sample from patient #7 contained a combination of swollen sperm heads, abnormal mitochondrial sheaths and residual cytoplasmic bodies. Other defects included nuclear vacuoles, cytoplasmic droplets still attached to the sperm midpiece, abnormal mitochondrial sheaths and large somatic cells present in the sample. Flow cytometry median reached 33.98% (compared with 18.43% in #1127). Previously diagnosed as a primary, tubal infertility, the sperm count was relatively good (222 million/ml), whereas motility was under average (42.3%) and no pregnancy was obtained. Ubiquitin assays suggest male factor contribution to this case previously diagnosed as maternal infertility.

The sample from patient #8 displayed a high number of misshaped sperm heads, suggesting a failure in the sperm nuclear condensation or differentiation of the perinuclear theca. Some abnormal mitochondrial sheaths and cells were observed, as well. The median value in flow cytometry was very high (39.24% vs. 22.88% in #1127). This was an unexplained infertility with relatively good sperm count (173 million/ml) and motility (67.6%), good fertilization rate (66.7%) and a low cleavage rate (27.3%). No pregnancy was obtained and ubiquitin data clearly indicate male factor infertility.

Ubiquitinated somatic cells, probably leukocytes, were detected in the sample of patient #9. Other abnormalities included round and elongated spermatids and globozoospermic sperm present in the ejaculate. The median flow cytometry value (35.23%) almost doubled that of a control sample #1127 (18.43%). Infertility was previously diagnosed as tubal, with relatively low sperm count (70 million/l) and average motility (54.2%). While a pregnancy was obtained, ubiquitin assays suggest the contribution of male factor infertility.

The sperm sample of patient #10 contained ubiquitinated sperm with lasso tails and nuclear vacuoles, and some residual cytoplasmic bodies were observed, as well. Both male and female factor infertility was previously diagnosed and is corroborated by ubiquitin assays. While the sperm count was good (145 million/ml), motility was only 25.2%. The remaining motile sperm yielded identical cleavage and fertilization rates (66.7%) and a pregnancy was obtained.

Patient #11 had a very good sperm sample with relatively few ubiquitinated sperm in which no predominant abnormality was detected, while the abnormalities described in other cases were occasionally found. Accordingly, the case was previously diagnosed as tubal infertility and fertilization and cleavage rates were excellent (both 100%), with an average sperm count (101 million/ml) and motility (48%). No pregnancy was obtained.

The sample from patient #12 had mostly morphologically normal sperm with relatively few ubiquitinated sperm cells. The major defect observed was nuclear vacuoles. Median (21.29%) was close to that of control #1127 (18.43%). Sperm parameters were good (189 million/ml; 87.3% motility). In view of both the excellent results obtained in the ubiquitin assays and good cleavage rates after IVF (50%), male factor is less likely to contribute this case of unexplained infertility, where no pregnancy was obtained.

Surprisingly, the major defect observed in the sample from patient #13 was the presence of twin sperm and sperm with two heads or two tails. Median for flow cytometry was only 20.54%, as compared to 18.43% in #1127, while a substantial shift and increase in the distribution and number of highly fluorescent cells was observed. Presence of ubiquitinated twin sperm may account for relatively low motility (47%), while other parameters were excellent (216 million spernm/ml). The case was pronounced idiopathic with 0% fertilization and cleavage rates after IVF and no pregnancy. With the exception of a good median value in flow cytometry, the ubiquitin assays suggest male factor infertility, further supported by 0% fertilization and cleavage rates.

Patient #14 had a relatively good sample with a major defect being broken and lasso tails. This man had the best flow cytometry median among all men screened (11.97% vs. 17.15% in fertile donor #1127). The couple was diagnosed-with tubal infertility, the fertilization and cleavage rates were average/good (57.1 and 42.9% respectively), and the motility rate was average (45.6%) with a good sperm count of 174 million/ml. There was no pregnancy and ubiquitin data suggest that this was not contributed by male factor.

Patient #15 had a mixture of various defect in his sperm sample, which included lasso tails, swollen heads, nuclear vacuoles, cells, residual cytoplasm and abnormal mitochondrial sheaths. The flow cytometry median value was 33.98% (vs. 22.88% in #1127) and a shift in the distribution of highly fluorescent cells was observed. This case was previously diagnosed as idiopathic with good sperm parameters (140 million/ml; 78% motility). However, ubiquitin assays point to a male factor infertility and no pregnancy was obtained.

Abnormal, lasso and twin sperm tails were the prevailing defects in the sample from patient #16, while other defects included malformed sperm heads and cells present in ejaculate. Both tubal and male factor infertility were diagnosed previously and corroborated by ubiquitin data as well as by low motility (33% at 213 million sperm/ml) and 0% fertilization and cleavage rates. No pregnancy was obtained.

The major defect in the sample from patient #17 was the presence of nuclear vacuoles, although globozoospermy and residual cytoplasmic droplets were also observed. The case was previously diagnosed as unexplained and the low cleavage rate (25%) was contradicted by good fertilization rate (83.3%) and sperm parameters (184 million/ml; 73.6% motility). Ubiquitin data suggest male factor contribution (partial globozoospermy), although female factor cannot be ruled out.

While the supply of samples permitted, ELISA assays were conducted on sperm of some patients. In a representative run (the results of which are presented in Table 4), the relative absorbance values for patients 3, 4, 6, 8, 9, 13 and 14 corroborated the data obtained by immunofluorescence and flow cytometry.

TABLE 4

ELISA Results

| Sample | $OD_{405}$ value $2.2 \times 10^6$ dilution | $OD_{405}$ value $2.2 \times 10^4$ dilution |
|---|---|---|
| 1018 | 0.181 | 0.199 |
| 3 | 0.212 | 0.274 |
| 4 | 0.229 | 0.291 |
| 6 | 0.200 | 0.236 |
| 8 | 0.171 | 0.193 |
| 14 | 0.174 | 0.196 |

Each of the three assays performed on the patients' sperm samples provides valuable information about the samples. The main value of the inmrunofluorescence assay is its ability to determine which particular types of sperm defects prevail in the sample. This is useful for clinicians planning strategies for further treatment. For example, irmnunofluorescence assay revealed globozoospermy in patient #1, which is an indication for ICSI (intracytoplasmic sperm injection) combined with artificial egg activation. In many cases, immunofluorescence methods can also provide quantitative data by allowing rapid detection of an elevated number of ubiquitinated sperm, somatic and spermatogenic cells, and residual cytoplasm. Though the immunofluorescence assay is relatively subjective and relies on the judgement of the evaluator, it can be complemented by flow cytometry and ELISA assays, to provide objective, unbiased quantification of ubiquitin titer in sperm samples.

In patients #3, 13, 15, 17, relatively good sperm count and motility, fertilization and cleavage parameters did not support male factor infertility, while ubiquitin data strongly supported a male contribution to these unexplained cases. This is probably due to the fact that motile sperm isolated from such ejaculates and devoid of the ubiquitinated abnormal spermatozoa by gradient centrifugation or swim up yield good fertilization rates. The ubiquitinated sperm present in the ejaculate may however interfere with motility and/or fertilizing ability of such sperm after coitus. Thus, fertilization and cleavage rates in vitro may not be sufficient for the diagnosis of male factor infertility in such unexplained cases. It is also possible that the superfluous ubiquitin present on the surface of even the motile spermatozoa of such men can be carried over to the egg after natural fertilization (and ICSI) and target such sperm cell to the egg proteolytic machinery, thus effectively preventing further embryonic development.

It is clear that the methods of the present invention provide an improved assay systems for analysis of male fertility. The detection and measurement of ubiquitinated sperm in a sample is an objective assay that is far more precise and more easily repeated than the subjective assays currently in use. In addition, these assays detect sperm with normal morphology that may actually be damaged. Furthermore, the assays are sufficiently robust that they are not impacted by damage caused by handling of the samples.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in reproductive physiology, immunology, immunochemistry, cell biology, and biochemistry or related fields are intended to be within the scope of the following claims.

What is claimed is:

1. A method for assaying fertility in an animal comprising:
   a) providing a semen sample comprising sperm, wherein at least a portion of said sperm are suspected of being ubiquitinated;
   b) measuring surface ubiquitination of sperm in said sample; and
   c) correlating said measured surface ubiquitination of sperm with fertility or infertility, wherein increased levels of ubiquitination are indicative of decreased rates of fertility.

2. The method of claim 1, wherein said semen sample is from a bovine.

3. The method of claim 1, wherein said semen sample is from a human.

4. The method of claim 1, wherein said measuring comprises:
   d) providing an antibody that binds to ubiquitin; and
   e) combining said semen sample with said antibody under conditions wherein said antibody binds to said ubiquitinated sperm.

5. The method of claim 4, wherein said antibody is selected from the group consisting of MAB 1510, AB 1690, Ubi-1, MK-11-3, MK-12-3, UCBA798/R5H, KM691, UG 9510, and U-5504.

6. The method of claim 4, wherein said antibody is labelled.

7. The method of claim 4, wherein said measuring further comprises determining said surface ubiquitination of sperm in said sample by flow cytometry.

8. The method of claim 4, wherein said measuring step further comprises determining said amount of ubiquitin in said sample by enzyme-linked immunosorbant assay.

9. The method of claim 4, wherein said measuring step further comprises determining said amount of ubiquitin in said sample by quantitating the number of ubiquitinated sperm.

10. The method of claim 4, further comprising detecting said antibody that binds to ubiquitin by binding to said antibody a second labelled antibody under conditions such that said second antibody bound to said antibody is detectable.

11. The method of claim 4, further comprising the step of:
    f) comparing said surface ubiquitination of sperm in said sample with surface ubiquitination of sperm in a control semen sample from a donor of known fertility.

12. The method of claim 1, wherein said measuring step further comprises determining said surface ubiquitination of sperm in said sample by enzyme-linked immunosorbant assay.

13. A method for assaying fertility in an animal comprising:
    a) providing
       i) a test semen sample containing sperm, wherein at least a portion of the sperm are suspected of being ubiquitinated; and
       ii) an antibody that binds to ubiquitin;
    b) combining said semen sample with said antibody under conditions wherein said antibody binds to said ubiquitinated sperm; and
    c) measuring the surface ubiquitination of sperm in said sample, wherein increased levels of ubiquitination are indicative of decreased rates of fertility.

14. The method of claim 13, wherein said semen sample is from a bovine.

15. The method of claim 13, wherein said semen sample is from a human.

16. The method of claim 13, wherein said antibody is selected from the group consisting of MAB 1510, AB 1690, Ubi-1, MK-11-3, MK-12-3, UCBA798/R5H, KM691, UG 9510, and U-5504.

17. The method of claim 13, wherein said antibody is labelled.

18. The method of claim 13, wherein said measuring further comprises determining said surface ubiquitination of sperm in said sample by flow cytometry.

19. The method of claim 13, wherein said measuring step further comprises determining said surface ubiquitination of sperm in said sample by counting the number of ubiquitinated and non-ubiquitinated sperm in said sample.

20. The method of claim 13, further comprising step
    d) calculating a value corresponding to said surface ubiquitination of sperm in said sample and comparing said value to a second value obtained from a donor of known fertility, wherein a higher value of ubiquitination in said test semen sample as compared to said control sample is indicative of infertility.

21. A kit for assaying fertility in an animal comprising:
a) a first container containing an antibody that binds to ubiquitin in surface of sperm cells, and wherein in assaying for fertility in an animal, binding of the antibody to ubiquitin on the surface of sperm cells at increased levels provides an indication of decreased rates of fertility; and
b) a control semen sample from a donor of known fertility.

22. The kit of claim 21, wherein said antibody that binds to ubiquitin is selected from the group consisting of MAB 1510, AB 1690, Ubi-1, MK-11-3, MK-12-3, UCBA798/R5H, KM691, UG 9510, and U-5504.

23. The kit of claim 22, further comprising a labelled second antibody that binds to said antibody that binds ubiquitin.

24. The kit of claim 21, comprising instructions for assaying fertility in an animal.

* * * * *